United States Patent

Nishihira et al.

[11] Patent Number: 5,037,982
[45] Date of Patent: Aug. 6, 1991

[54] METHOD OF PURIFYING 2-METHYL-4-AMINO-5-AMINOMETHYL-PYRIMIDINE

[75] Inventors: Keigo Nishihira, Ube; Masayoshi Yamashita, Tokyo; Hiroshi Yoshida, Ube, all of Japan

[73] Assignee: Ube Industries, Ltd., Ube, Japan

[21] Appl. No.: 408,771

[22] Filed: Sep. 18, 1989

Related U.S. Application Data

[62] Division of Ser. No. 186,167, Apr. 26, 1988, Pat. No. 4,892,948.

[30] Foreign Application Priority Data

May 15, 1987 [JP] Japan .................. 62-117062

[51] Int. Cl.$^5$ .......................................... C07D 239/02
[52] U.S. Cl. ...................................................... 544/326
[58] Field of Search .......................................... 544/326

[56] References Cited

U.S. PATENT DOCUMENTS 4,278,793  7/1981  Durckheimer et al. ............ 546/183
4,788,198  11/1988  Grozinger et al. ................ 544/336

FOREIGN PATENT DOCUMENTS 59-46274  3/1984  Japan .

OTHER PUBLICATIONS

Yakugaku Zasshi (The Journal of Pharmacology) 71, 720 1215 (1951).

Primary Examiner—Johann Richter
Attorney, Agent, or Firm—Frishauf, Holtz, Goodman & Woodward

[57] ABSTRACT

A method of purifying 2-methyl-4-amino-5-aminomethylpyrimidine by heating the carbonate thereof. Preferably the heating is carried out in water or a specified solvent.

13 Claims, 1 Drawing Sheet

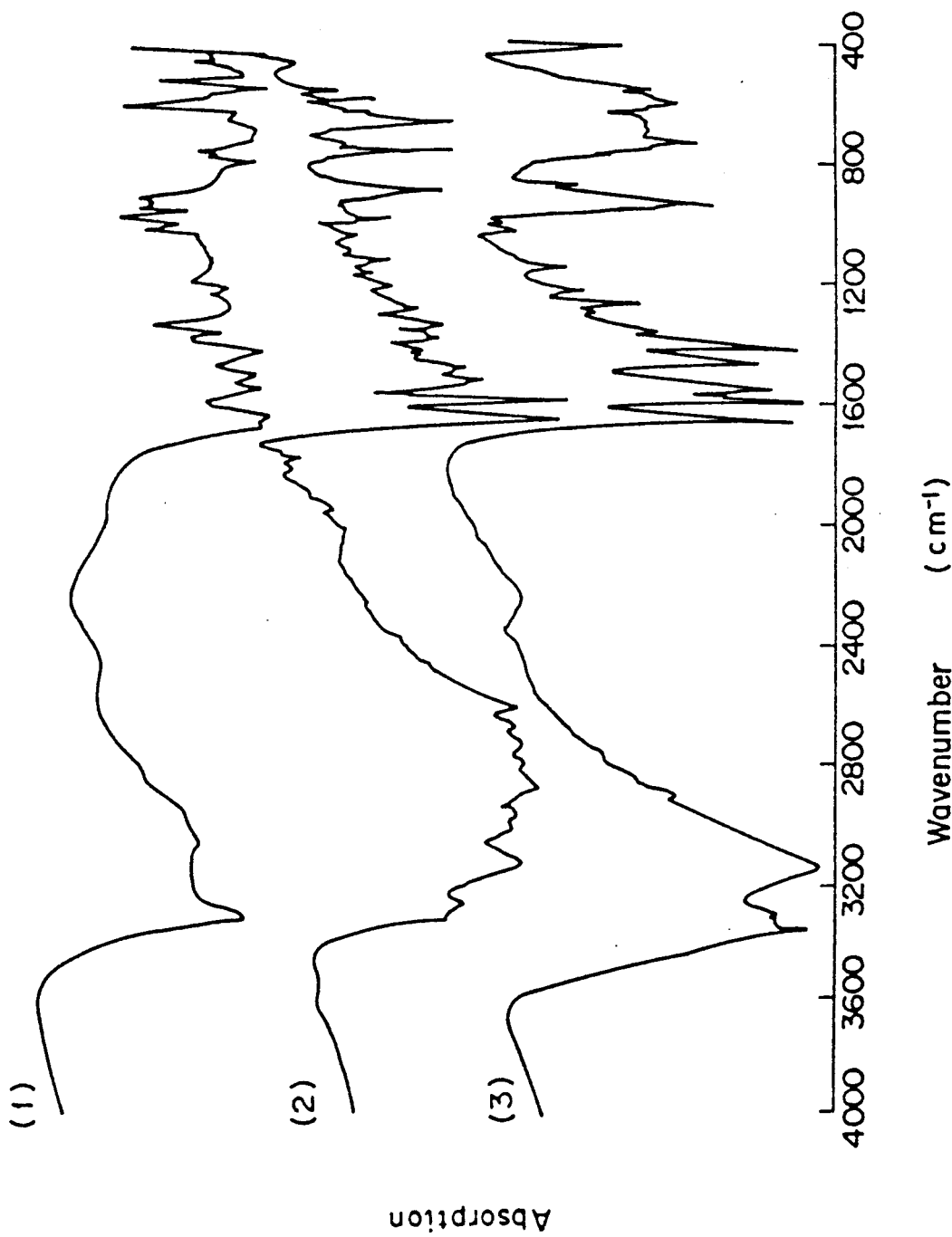

METHOD OF PURIFYING 2-METHYL-4-AMINO-5-AMINOMETHYLPYRIMIDINE

This is a division of application Ser. No. 07/186,167 filed Apr. 26, 1988 now U.S. Pat. No. 4,892,948.

BACKGROUND OF THE INVENTION

This invention relates to a novel 2-methyl-4-amino-5-aminomethylpyrimidine carbonate which is useful as an intermediate for producing vitamine $B_1$, a process for preparing the same and a method of purification of 2-methyl-4-amino-5-aminomethylpyrimidine using the same.

As a method for producing vitamine $B_1$, there has generally be known the method in which vitamine $B_1$ is synthesized from 2-methyl-4-amino-5-aminomethylpyrimidine, carbon disulfide and 2-acetylbutyrolactone, as described in Yakugaku Zasshi (The Journal of Pharmacology) 71, 720 1215 (1951).

SUMMARY OF THE INVENTION

This invention provides a 2-methyl-4-amino-5-aminomethylpyrimidine carbonate which is a novel compound, a process for preparing the same which comprises subjecting 2-methyl-4-amino-5-aminomethylpyrimidine to reaction with carbon dioxide in a lower aliphatic alcohol, and a simple method of purification of 2-methyl-4-amino-5-aminomethylpyrimidine by using the carbonate thereof.

BRIEF DESCRIPTION OF THE DRAWING

FIG. 1 shows IR spectrum of 2-methyl-4-amino-5-aminomethylpyrimidine carbonate obtained in Example 1.

DESCRIPTION OF THE PREFERRED EMBODIMENTS

This invention will be described below by referring to preparation examples.

First, a desired amount of 2-methyl-4-amino-5-aminomethylpyrimidine is dissolved in a lower aliphatic alcohol.

The 2-methyl-4-amino-5-aminomethylpyrimidine used herein is a known compound, and can be produced, for example, according to the following method described in Japanese Provisional Patent Publication No. 46274/1984:

2-Alkyl-4-amino-5-aminomethylpyrimidine derivatives can be prepared by catalytic reaction of 2-alkyl-4-amino-5-dialkoxymethylpyrimidine of Formula (I):

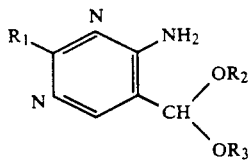

wherein $R_1$, $R_2$ and $R_3$ is a lower alkyl group such as methyl, ethyl, propyl and butyl, and $R_1$, $R_2$ and $R_3$ each may be the same or different from each other, with $H_2$ in ammonia aqueous solution in the presence of an acid and a reducing catalyst.

The compound (I) is easily synthesized by reaction of 2-alkoxy-methylene-3,3-dialkoxypropanenitriles or 2-dialkoxymethyl-3,3-dialkoxypropane nitriles with acetamidine. Pd, Pt, Rh, Ru, Ni, Co, Fe, Cu or Cr is used as the reducing catalyst in an amount of 0.001 to 3 g atom, preferably 0.002 to 2 g atom of these metals for 1 mole of compound (I). Mineral acids such as HCl, $H_2SO_4$ and $H_3PO_4$ or an organic acid such as acetic acid and p-toluenesulfonic acid are used as the acids.

The lower aliphatic alcohol may include, for example, methanol, ethanol, n-propanol, isopropanol, n-butanol, isobutanol, sec-butanol, tert-butanol, etc.

The amount of the lower aliphatic alcohol may not particularly be limited so long as it is a sufficient amount for the complete dissolution of the 2-methyl-4-amino-5-aminomethylpyrimidine. However, in order to facilitate handling of the slurry 2-methyl-4-amino-5-aminomethyl-pyrimidine carbonate formed, the alcohol may preferably be used in 3-fold amount or more relative to the amount of the 2-methyl-4-amino-5-aminomethylpyrimidine. It should be noted, however, that employment of large excess of a lower aliphatic alcohol will result in the increase in energy consumption required for the collection of the same and also in the increase of the cost for the collection. Accordingly, the amount of the alcohol to be used should preferably be determined in view of the workability during the production and cost therefor.

The carbon dioxide to be used in the reaction should be in a stoichiometric amount or more, and preferably in an amount of 1.10 moles or more per 1 mol of 2-methyl-4-amino-5aminomethylpyrimidine.

The reaction is carried out by blowing carbon dioxide into a solution of 2-methyl-4-amino-5-aminomethylpyrimidine dissolved in a lower aliphatic alcohol. In the above reaction, the blowing rate is preferably about 1 to 10 moles/hour. Also, such reaction is carried out at a temperature of 0° to 60° C., preferably 0° to 40° C. under normal or applied pressure.

The mode of reaction to be applied may be any of batchwise, semi-batchwise and continuous method.

By reacting 2-methyl-4-amino-5-aminomethylpyrimidine with carbon dioxide as described above, a 2-methyl-4-amino-5-aminomethylpyrimidine carbonate can easily be precipitated. Subsequently, said carbonate precipitated is separated and collected by a means of an appropriate solid-liquid separating operation, such as filtration or centrifugation. The above described carbonate has much less solubility in a lower alcohol (for example, solubility in methanol: about 1.0% at 50° C.) than other acid salt of the pyrimidine (for example, solubility of hydrochloride salt in methanol: about 3.3% at 50° C.), and thus it is advantageously possible to reduce loss in the end-product due to its dissolution into the solvent during purification process. The solid portion thus collected is then, if necessary, subjected to treatment such as washing, drying, etc. to obtain 2-methyl-4-amino-5-aminomethylpyrimidine carbonate of high purity.

While the 2-methyl-4-amino-5-aminomethylpyrimidine carbonate can be obtained as described above, the process for preparing the above 2-methyl-4-amino-5-aminomethylpyrimidine carbonate can also be used as a means for purifying 2-methyl-4-amino-5-aminomethylpyrimidine. No satisfactory process for purifying 2-methyl-4-amino-5-aminomethylpyrimidine has so far been available. However, 2-methyl-4-amino-5-aminomethylpyrimidine of high purity can easily be obtained by employing the process of production according to this invention as a purifying means. The method of purifying 2-methyl-4-amino-5-aminomethylpyrimidine employing the present preparation process will be described below.

More specifically, using, for example, 2-methyl-4-amino-5-aminomethylpyrimidine of low purity as obtained according to the process described in Japanese Provisional Patent Publication No. 46274/1984, a 2-methyl-4-amino-5-aminomethylpyrimidine carbonate of high purity is produced by employing the present preparation process. Then, to the resulting 2-methyl-4-amino-5-aminomethylpyrimidine carbonate is added water or at least one organic solvent selected from aliphatic alcohols as described above, benzene, toluene, xylene, etc. in 0.5 to 10 fold amount relative to the 2-methyl-4-amino-5-aminomethylpyrimidine carbonate obtained, followed by heating at 60° to 150° C.; or further about 1.0 to 2.0 equivalent amount of an alkali metal hydroxide can be added relative to the 2-methyl-4-amino-5-aminomethylpyrimidine carbonate, followed by heating at 10° to 40° C., to form easily 2-methyl-4-amino-5-aminomethylpyrimidine.

Subsequently, the 2-methyl-4-amino-5-aminomethylpyrimidine can be separated and collected, and if necessary, followed by treatment such as washing, drying, etc. to obtain a 2-methyl-4-amino-5-aminomethylpyrimidine of high purity.

Meanwhile, it is necessary to convert the acid salt of the pyrimidine to a free form, when the acid salt is used for producing vitamine $B_1$, and for this purpose neutralization with a strong base has generally been employed. However, in case of the carbonate, there is a great advantage that the free form can be obtained by heating only as described above without addition of any strong base.

[EXAMPLES]

Example 1

A solution of 50 g of crude 2-methyl-4-amino-5-aminomethylpyrimidine (purity: 95.0%, 0.344 mole) dissolved in 250 g of methanol was charged into a four-necked flask equipped with a stirrer, an introducing tube for carbon dioxide, a reflux condenser and a thermometer, followed by maintaining the temperature of the solution at 20° C. Subsequently, 64 g (1.45 mole) of carbon dioxide was blown into the solution over about one hour and the reaction was carried out to precipitate a white crystal of a 2-methyl-4-amino-5-aminomethylpyrimidine carbonate with extreme easiness. Then, the resulting crystal was filtered off, washed with a small amount of methanol, and dried at 20° C. until it may have constant weight to give 61.8 g of 2-methyl-4-amino-5-aminomethylpyrimidine carbonate.

When the 2-methyl-4-amino-5-aminomethylpyrimidine carbonate thus obtained was determined by use of a liquid chromatography, it was found that it contains 46.5 g (0.337 mole) in terms of 2-methyl-4-amino-5-aminomethylpyrimidine. Accordingly, it was found that the recovery was 98.0% in terms of 2-methyl-4-amino-5-aminomethylpyrimidine and the purity of the 2-methyl-4-amino-5-aminomethylpyrimidine carbonate was 99.2%. Further, the elemental analysis value of the 2-methyl-4-amino-5-aminomethylpyrimidine carbonate is given below and the IR spectrum thereof (in KBr) is shown in FIG. 1.

|  | C | H | N |
|---|---|---|---|
| Theoretical value (%) | 46.15 | 5.49 | 30.77 |
| Found value (%) | 46.22 | 5.69 | 30.46 |

Example 2

Into the same four-necked flask as used in Example 1 was charged a solution of 30.0 g (purity: 96.2 %, 0.209 mole) of crude 2-methyl-4-amino-5-aminomethylpyrimidine dissolved in 300 g of isopropanol, followed by maintaining the temperature of the solution at 10° C. Subsequently, 44 g (1 mole) of carbon dioxide was blown into the solution over about 2 hours and the reaction was carried out to precipitate a white crystal of 2-methyl-4-amino-5-aminomethylpyrimidine carbonate with extreme easiness. Then, the resulting crystal was filtered off, washed with a small amount of isopropanol, and dried in vacuo at 20° C. until it may have constant weight to obtain 37.8 g of 2-methyl-4-amino-5-aminomethylpyrimidine carbonate.

When the 2-methyl-4-amino-5-aminomethylpyrimidine carbonate thus obtained was determined by use of a liquid chromatography, it was recognized that it contains 28.4 g (0.206 mole) in terms of 2-methyl-4-amino-5-aminomethylpyrimidine. Accordingly, it was found that the recovery was 98.6% in terms of 2-methyl-4-amino-5-aminomethylpyrimidine and the purity of the 2-methyl-4-amino-5-aminomethylpyrimidine carbonate was 99.0%.

An amount of 170 g of isopropanol was added to 30.0 g of the 2-methyl-4-amino-5-aminomethylpyrimidine carbonate thus obtained, followed by heating at about 85° C. for 180 minutes to give 2-methyl-4-amino-5-aminomethylpyrimidine with purity of 99.0%.

Because of the excellent crystallizability of the 2-methyl-4-amino-5-aminomethylpyrimidine carbonate of this invention, it can be obtained easily using a simple operation. Also, since the 2-methyl-4-amino-5-aminomethylpyrimidine carbonate according to this invention is neutral, it is excellent in that it can provide easy handling compared with the 2-methyl-4-amino-5-aminomethylpyrimidine which is highly alkaline and may cause chemical damage on the hand or the like, such as itching, eruption, etc. through contact therewith and that it can be transported and handled easily because it is available as a powder crystal of homogeneous quality.

Further, purity of 2-methyl-4-amino-5-aminomethylpyrimidine can easily be improved by employing the present preparation process as a method of purification of the same.

We claim:

1. A method of purification of crude 2-methyl-4-amino-5-aminomethylpyrimidine comprising reacting said crude compound with carbon dioxide in a solvent to form 2-methyl-4-amino-5-aminomethylpyrimidine carbonate which is recovered as a precipitate and heating said carbonate to a temperature of 60° to 150° C. to obtain a purified 2-methyl-4-amino-5-aminomethylpyrimidine, said solvent being selected from the group consisting of water, methanol, ethanol, n-propanol, isopropanol, n-butanol, isobutanol, sec-butanol, tert-butanol, benzene, toluene and xylene.

2. A method of purification of crude 2-methyl-4-amino-5-aminomethylpyrimidine comprising reacting at a temperature between 0° to 60° C. said crude compound with carbon dioxide in a solvent to form 2-methyl-4-amino-5-aminomethylpyrimidine carbonate which is recovered as a precipitate and heating said carbonate to obtain a purified 2-methyl-4-amino-5-aminomethylpyrimidine, said solvent being an alcohol selected from the group consisting of methanol, ethanol, n-propanol, isopropanol, n-butanol, isobutanol, sec-butanol, and tert-butanol.

3. A method of purification of crude 2-methyl-4-amino-5-aminomethylpyrimidine comprising reacting at a temperature of 0° to 60° C. said crude compound with carbon dioxide in a solvent to form 2-methyl-4-amino-5-aminomethylpyrimidine carbonate which is recovered as a precipitate and heating said carbonate to obtain a purified 2-methyl-4-amino-5-aminomethylpyrimidine, said carbon dioxide being in an amount of at least 1.1 moles per mole of said 2-methyl-4-amino-5-aminomethylpyrimidine and being fed in an amount of from 1 to 10 moles per hour, said solvent being an alcohol selected from the group consisting of methanol, ethanol, n-propanol, isopropanol, n-butanol, isobutanol, sec-butanol, and tert-butanol.

4. The method according to claim 1, wherein said solvent is in an amount of from 0.5 to 10 times the amount of said 2-methyl-4-amino-5-aminomethylpyrimidine carbonate.

5. The method according to claim 4, wherein 1 to 2 equivalent amount of an alkali metal hydroxide is added relative to the 2-methyl-4-amino-5-aminomethylpyrimidine carbonate, followed by heating at 10° to 40° C.

6. The method according to claim 4, wherein said solvent is methanol or isopropanol.

7. The method according to claim 1, wherein said solvent is an alcohol selected from the group consisting of methanol, ethanol, n-propanol, isopropanol, n-butanol, isobutanol, sec-butanol, and tert-butanol.

8. The method according to claim 7, wherein said alcohol is in an amount three times that of said 2-methyl-4-amino-5-aminomethylpyrimidine.

9. The method according to claim 7, wherein said carbon dioxide is in an amount of at least 1.1 moles per mol of 2-methyl-4-amino-5-aminomethylpyrimidine.

10. The method according to claim 7, wherein said carbon dioxide is fed in an amount of from 1 to 10 moles/hour.

11. The method according to claim 3, wherein said alcohol is in an amount three times that of said 2-methyl-4-amino-5-aminomethylpyrimidine.

12. The method according to claim 3, wherein said heating of said carbonate is at a temperature of 60° to 150° C.

13. The method according to claim 12, wherein said alcohol in which the reaction with carbon dioxide is carried out and said solvent in which the carbonate is heated are the same and is methanol or isopropanol.

* * * * *